US008506621B2

(12) United States Patent
Agnew et al.

(10) Patent No.: US 8,506,621 B2
(45) Date of Patent: *Aug. 13, 2013

(54) FLOW-DEFLECTING MEDICAL DEVICE

(75) Inventors: Charles W. Agnew, West Lafayette, IN (US); Ram H. Paul, Jr., Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/355,959

(22) Filed: Jan. 23, 2012

(65) Prior Publication Data

US 2012/0123518 A1  May 17, 2012

Related U.S. Application Data

(63) Continuation of application No. 12/350,456, filed on Jan. 8, 2009, now Pat. No. 8,100,962.

(60) Provisional application No. 61/019,751, filed on Jan. 8, 2008.

(51) Int. Cl.
*A61F 2/06* (2013.01)

(52) U.S. Cl.
USPC ........................................ 623/1.24; 623/1.16

(58) Field of Classification Search
USPC ........... 623/1.24, 1.26, 2.12, 2.14, 2.16–2.18; 609/4
See application file for complete search history.

(56) References Cited

U.S. PATENT DOCUMENTS

| | | | |
|---|---|---|---|
| 4,643,732 | A | 2/1987 | Pietsch et al. |
| 5,769,780 | A | 6/1998 | Hata et al. |
| 6,221,091 | B1 | 4/2001 | Khosravi |
| 6,602,286 | B1 | 8/2003 | Strecker |
| 6,752,828 | B2 | 6/2004 | Thornton |
| 8,100,962 | B2 | 1/2012 | Agnew et al. |
| 2001/0025197 | A1 | 9/2001 | Shu et al. |
| 2002/0065554 | A1 | 5/2002 | Streeter |
| 2003/0033009 | A1 | 2/2003 | Gabbay |
| 2003/0040792 | A1 | 2/2003 | Gabbay |
| 2003/0055496 | A1 | 3/2003 | Cai et al. |
| 2003/0130726 | A1 | 7/2003 | Thorpe et al. |
| 2003/0208261 | A1 | 11/2003 | Thorpe et al. |
| 2004/0225352 | A1 | 11/2004 | Case et al. |
| 2005/0010287 | A1 | 1/2005 | Macoviak et al. |
| 2005/0143807 | A1 | 6/2005 | Pavcnik et al. |
| 2005/0187614 | A1 | 8/2005 | Agnew |
| 2006/0058889 | A1 | 3/2006 | Case et al. |
| 2007/0288086 | A1 | 12/2007 | Kalmann et al. |

FOREIGN PATENT DOCUMENTS

EP         0520126        12/1992

*Primary Examiner* — Thomas J Sweet
*Assistant Examiner* — Tiffany Shipmon
(74) *Attorney, Agent, or Firm* — Buchanan Nipper

(57) ABSTRACT

The disclosure relates to a flow-deflecting medical device comprising a support structure and two flow-deflecting members attached to the support structure. The first flow-deflecting member is movable to a position in which it contacts and substantially seals against the second flow-deflecting member.

20 Claims, 9 Drawing Sheets

FLOW-DEFLECTING MEDICAL DEVICE

RELATED APPLICATIONS

This non-provisional patent application is a continuation of U.S. Non-provisional patent application Ser. No. 12/350,456, filed on Jan. 8, 2009 and which claims priority to U.S. Provisional Patent Application No. 61/019,751, filed on Jan. 8, 2008. The entire contents of each of these related applications are hereby incorporated by reference into this disclosure.

BACKGROUND OF THE INVENTION

The venous system includes a multitude of one-way bicuspid valves that permit substantially unidirectional blood to flow toward the heart. These valves are particularly important in the lower extremities to prevent the pooling of blood. When the leaflets of the bicuspid valves fail to close properly, the valves are considered "incompetent" as they permit leakage of retrograde flow resulting in the abatement of flow towards the heart.

This potentially serious condition is known as "chronic venous insufficiency." Symptoms can progress from unsightly "spider" or varicose veins to skin discoloration and painful skin ulcerations. The etiology of venous insufficiency is multifactorial, including a past history of thrombotic events, chronic venous stasis, and venous hypertension. Current treatments for venous insufficiency include elevation of the feet and compression stockings. While these can relieve symptoms, the underlying disease remains untreated. Surgical techniques also may be employed in which native valves can be bypassed or replaced with autologous sections of veins having functioning valves.

Various implantable medical devices and minimally invasive techniques for implantation of these devices have been developed to treat and repair undesirable conditions within body vessels. For example, implantable medical devices can function as a replacement venous valve, or improve the function of native valves by blocking or reducing retrograde flow. These devices are advantageously inserted intravascularly, for example from an implantation catheter.

Post-implantation thrombosis and platelet deposition on surfaces of endovascular prosthetic devices may occlude the conduit defined by the endovascular prosthesis or compromise the functionality of an implanted prosthetic valve by limiting the motion or responsiveness of moveable portions of the device. For example, stagnation of blood around implanted prosthetic devices may lead to fibrin deposition and formation of thrombosis, reducing the devices' functionality and possibly eventually occluding the body lumen.

SUMMARY

The present disclosure relates to a flow-deflecting medical device. The device comprises a support structure and at least one flow-deflecting member at least partially evertible between a first position and a second position. The flow-deflecting member comprises an antegrade flow-receiving surface and a retrograde flow-receiving surface. The flow-deflecting member further comprises a first portion coupled to the support structure and a second portion that is free of the support structure. In the first position, the flow-deflecting member's antegrade flow-receiving surface is contacted by antegrade flow, and the second portion is urged proximal to the first portion. In the second position, the flow-deflecting member's retrograde flow-receiving surface is contacted by retrograde flow, and the second portion is urged distal to the first portion, thereby receiving and advantageously redirecting retrograde flow therebelow.

A method of treating a body vessel valve-related condition also is provided. The method comprises implanting a flow-deflecting medical device comprising at least one flow-deflecting member proximal to a native valve, where the flow-deflecting member redirects retrograde flow onto the native valve.

Other systems, methods, features and advantages will be, or will become, apparent to one with skill in the art upon examination of the following figures and detailed description. It is intended that all such additional systems, methods, features and advantages be included within this description, be within the scope of the disclosure, and be protected by the following claims.

BRIEF DESCRIPTION OF THE DRAWINGS

The medical device may be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

DETAILED DESCRIPTION

Figure 1:
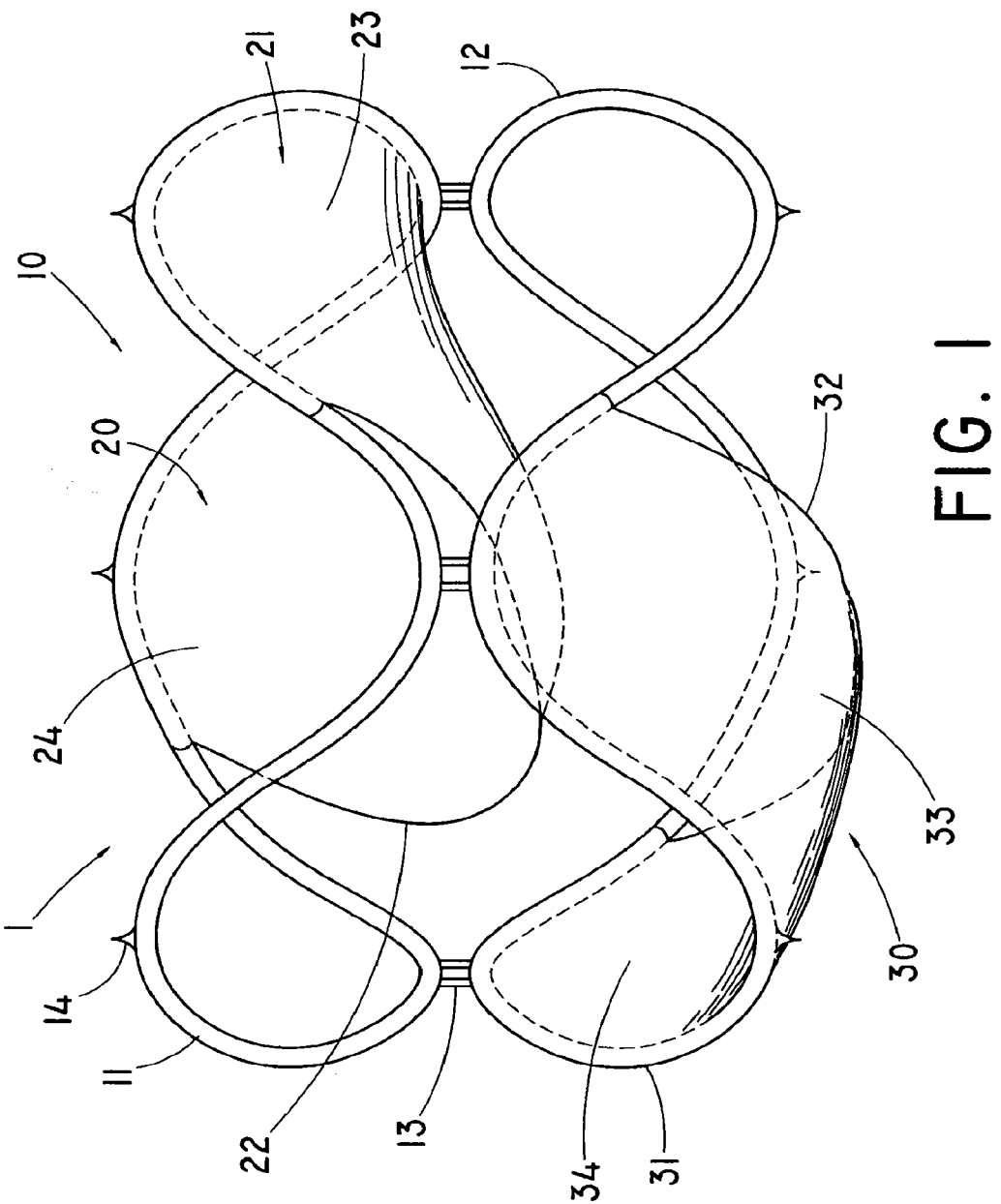
FIG. 1 is a perspective view of an exemplary flow-deflecting medical device.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can be used in the practice or testing of the present disclosure. All publications, patent applications, patents and other references mentioned herein are incorporated by reference in their entirety. The materials, methods, and examples disclosed herein are illustrative only and not intended to be limiting.

Definitions

The term "body vessel" means any tube-shaped body passage lumen that conducts fluid, including but not limited to blood vessels such as those of the human vasculature system, esophageal, intestinal, billiary, urethral and ureteral passages.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

The term "implantable" refers to an ability of a medical device to be positioned, for any duration of time, at a location within a body, such as within a body vessel. Furthermore, the terms "implantation" and "implanted" refer to the positioning, for any duration of time, of a medical device at a location within a body, such as within a body vessel.

The terms "distal" and "distally" refer to a location or direction that is, or a portion of a device that when implanted is further downstream in the direction of or with respect to blood flow. The terms "proximal" and "proximally" refer to a location or direction that is, or a portion of a device that when implanted is further upstream in the direction of or with respect to blood flow.

The term "support structure" refers to a structure that can be implanted, or adapted for implantation, within the lumen of a body vessel. The device support structure may have any suitable configuration, but is preferably a radially expandable structure comprising a plurality of struts and bends and enclosing an interior lumen.

The term "antegrade fluid flow" refers to the flow of fluid in a primary direction of normal movement within a body vessel. For example, in the venous system, antegrade fluid flow proceeds primarily toward the heart.

The term "retrograde fluid flow" refers to fluid flow in a direction opposite the primary (antegrade) direction of fluid flow. For example, in the venous system, retrograde fluid flow is primarily directed away from the heart.

The terms "about" or "substantially" used with reference to a quantity includes variations in the recited quantity that are equivalent to the quantity recited, such as an amount that is insubstantially different from a recited quantity for an intended purpose or function.

Flow-Deflecting Medical Devices

Flow-deflecting medical devices may have a variety of suitable configurations. In one example, the flow-deflecting medical device comprises a support structure and at least one flow-deflecting member. Flow-deflecting members are preferably configured to redirect and/or reduce the rate of retrograde fluid flow within a body vessel.

The flow-deflecting medical device may be any medical device that is introduced temporarily or permanently into the body for the prophylaxis or therapy of a medical condition. For example, such devices may include, but are not limited to, heart valve prostheses, venous valve prostheses, artificial organs such as artificial hearts, and ventricular assist devices. Typical subjects (also referred to herein as "patients") are vertebrate subjects (i.e., members of the subphylum cordata), including, mammals such as cattle, sheep, pigs, goats, horses, dogs, cats and humans.

Flow-Deflecting Members

Flow-deflecting medical devices comprise at least one flow-deflecting member attached to the medical device. Medical devices comprising at least one flow-deflecting member may be used to regulate fluid flow in a vein, for example to treat venous valve incompetency. For example, one or more medical devices comprising one or more flow-deflecting members may be implanted in a body vessel with incompetent native valves to provide a valve to replace the incompetent native valves. One or more flow-deflecting members can permit fluid to flow through a body vessel in a first direction while redirecting and/or reducing the rate of fluid flow in the opposite direction.

In one example, the flow-deflecting medical device may include a plurality of flow-deflecting members. FIG. 1 is a perspective view of a medical device comprising a support structure 10, a first flow-deflecting member 20, and a second flow-deflecting member 30. A first attached edge 21 of the first flow-deflecting member 20 is attached to a first support structure portion 11. A second free edge 22 of the first flow-deflecting member 20 is free of the support structure 10, permitting the first flow-deflecting member 20 to be responsive to the direction of fluid flow in a body vessel. The first flow-deflecting member has an antegrade flow-receiving surface 23 and a retrograde flow-receiving surface 24. For example, when the medical device is implanted in a body vessel, antegrade flow will contact the antegrade flow-receiving surface 23, and retrograde flow will contact the retrograde flow-receiving surface 24.

A first attached edge 31 of the second flow-deflecting member 30 is attached to a second support structure portion 12, located distal the first support structure portion 11. A second free edge 32 of the second flow-deflecting member 30 is free of the support structure 10, permitting the second flow-deflecting member 30 to be responsive to the direction of fluid flow in a body vessel. The second flow-deflecting member has an antegrade flow-receiving surface 33 and a retrograde flow-receiving surface 34. When the medical device is implanted in a body vessel, antegrade flow will contact the antegrade flow-receiving surface 33, and retrograde flow will contact the retrograde flow-receiving surface 34.

Figure 2A:
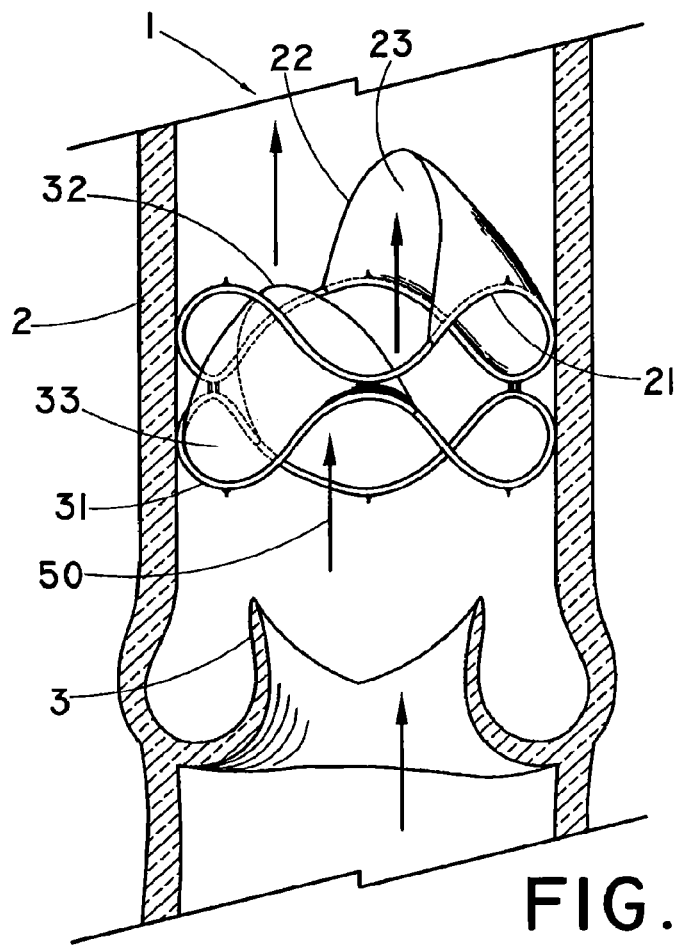
FIG. 2A is a partially sectioned view of a body vessel containing the flow-deflecting medical device of FIG. 1, located proximal to a native valve, in a first position.
Figure 2B:
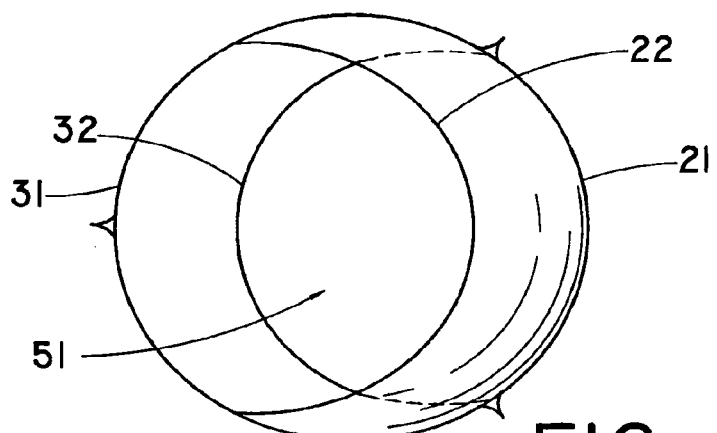
FIG. 2B is a top view of the FIG. 1 flow-deflecting member in the first position.
Figure 3A:
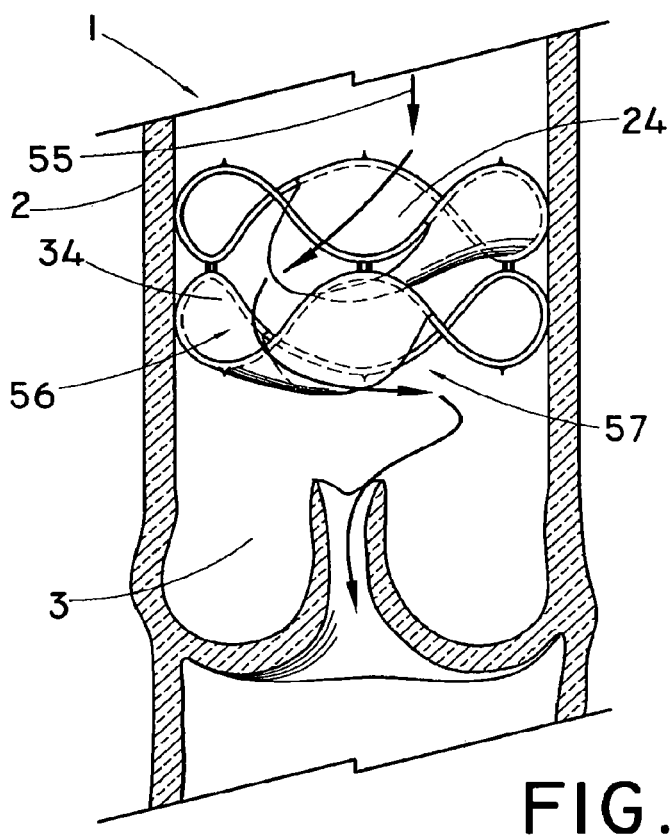
FIG. 3A is a partially sectioned view of a body vessel containing flow-deflecting medical device of FIG. 1, located proximal to a native valve, in a second position.

In one example, the first flow deflecting member 20 and the second flow deflecting member 30 are at least partially evertible between a first position shown in FIG. 2A, and a second position shown in FIG. 3A. In the first position, antegrade flow 50 contacts the antegrade flow-receiving surfaces 23 and 33, urging the flow-deflecting members 20 and 30, respectively, proximally in the body vessel. For example, in FIG. 2A, the free edges 22 and 32 of the first and second flow-deflecting members are urged proximal to the attached edges 21 and 31 by antegrade flow 50. With the first 20 and second 30 flow-deflecting members in the first position, a central orifice 51, shown in FIG. 2B, within the body vessel is created intermediate the flow deflecting member free edges 22, 32 such that antegrade flow within the body vessel is substantially unobstructed by the medical device.

Figure 3B:
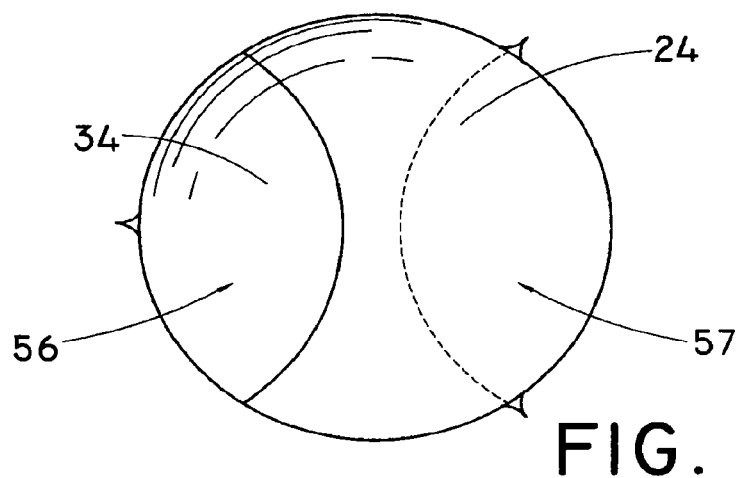
FIG. 3B is a top view of the FIG. 1 flow-deflecting member in the second position.

In the second position, retrograde flow 55 contacts the retrograde flow-receiving surfaces 24 and 34, urging the flow-deflecting members 20 and 30, respectively, distally in the body vessel. For example, in FIG. 3A, the free edges 22 and 32 of the first 20 and second 30 flow-deflecting members are urged distal to the attached edges 21 and 31 by retrograde flow 55. With the first 20 and second 30 flow-deflecting members in the second position, central orifice 51 is minimized, as shown in FIG. 3B, thereby delaying or slowing retrograde flow 55 and possibly reducing blood volume and head pressure on proximate native venous valves. The first and second flow-deflecting members are preferably configured to include sufficient slack and flexibility to evert and invert such that the central orifice 51 is sized to allow sufficient antegrade flow, while receiving and deflecting retrograde flow.

Figure 9A:
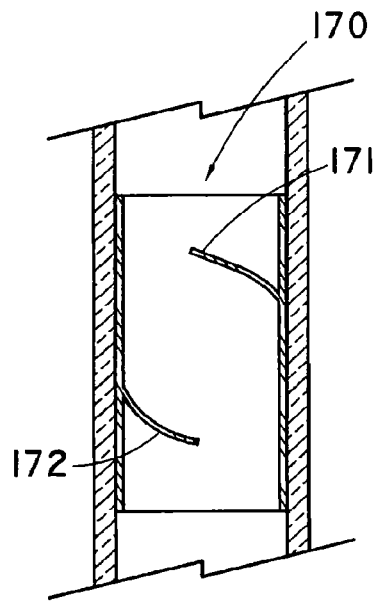
FIG. 9A is a partially sectioned view of a body vessel containing a flow-deflecting medical device, at equilibrium, having a first flow-deflecting member biased to a first position and a second flow-deflecting member biased to a second position.

In some examples, the flow deflecting member(s) may be biased to the first position or to the second position. For example, in FIG. 9A, the flow-deflecting medical device 170 includes a first flow deflecting member 171 biased to the first position and a second flow deflecting member 172 biased to the second position. In other examples, the second flow deflecting member 172 may be unbiased or biased to the first position.

Figure 9B:
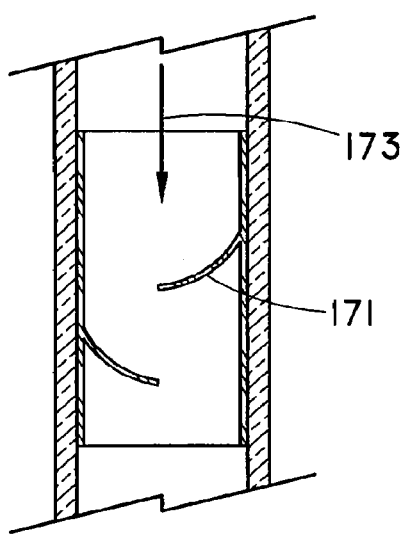
FIG. 9B is a partially sectioned view of a body vessel having retrograde fluid flow containing the flow-deflecting medical device of FIG. 9A.
Figure 9C:
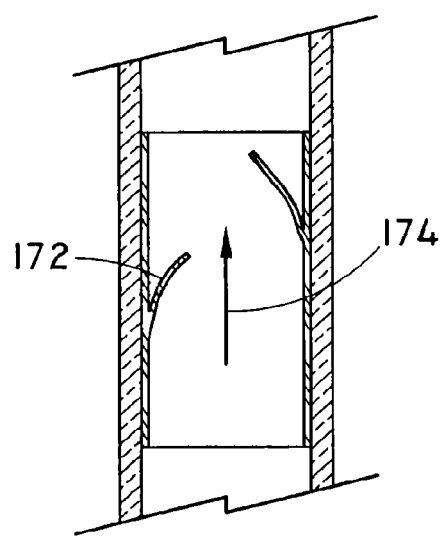
FIG. 9C is a partially sectioned view of a body vessel having antegrade fluid flow containing the flow-deflecting medical device of FIG. 9A.

Biased flow-deflecting members 171, 172 may have a biasing force less than the force exerted by the fluid flow in the vessel such that the biased flow deflecting members are responsive to fluid flow through a body vessel. For example, as shown in FIG. 9B, the first flow deflecting member 171 biased to the first position may have a biasing force that is less than the force exerted by retrograde flow 173. This permits the first flow deflecting member 171 to be urged to the second position by the retrograde flow 173 despite being biased to the first position. The second flow deflecting member 172 biased to the second position may have a biasing force that is less than the force exerted by antegrade flow 174. As shown in FIG. 9C, this permits the second flow deflecting member 172 to be urged to the first position by the antegrade flow 174 despite being biased to the second position. The flow deflecting medical device may also include flow deflecting members having varying flexibility. For example, a second flow deflecting member biased to the second position may be more flexible and responsive to fluid flow than a first flow deflecting member biased to the first position.

As further depicted in FIGS. 2A, 2B and 3A, 3B, the second flow-deflecting member 30 has an orientation different from the first flow-deflecting member 20 such that retrograde flow 55 is deflected by the first flow-deflecting member 20, through a remaining gap or orifice 56, onto the second flow-deflecting member 30, which directs it through a second orifice 57. In one example, the second flow-deflecting member 30 is oriented oppositely the first flow-deflecting member 20 so that the second orifice 57 is oriented about 180 degrees with respect to the first orifice 56. As such, the retrograde flow 55 assumes a serpentine path through the medical device.

The length that flow deflecting members extend into the body vessel may vary. The flow deflecting members may have a length between about 1% to about 100% of the vessel diameter. In one example, the first flow deflecting member length is between about 25% to about 75% of the vessel diameter. In another example, the second flow deflecting member is between about 25% % to about 75% of the vessel diameter. In a further example, both the first and second flow deflecting members have a length equal to about 55% to 75% of the vessel diameter.

Figure 4:
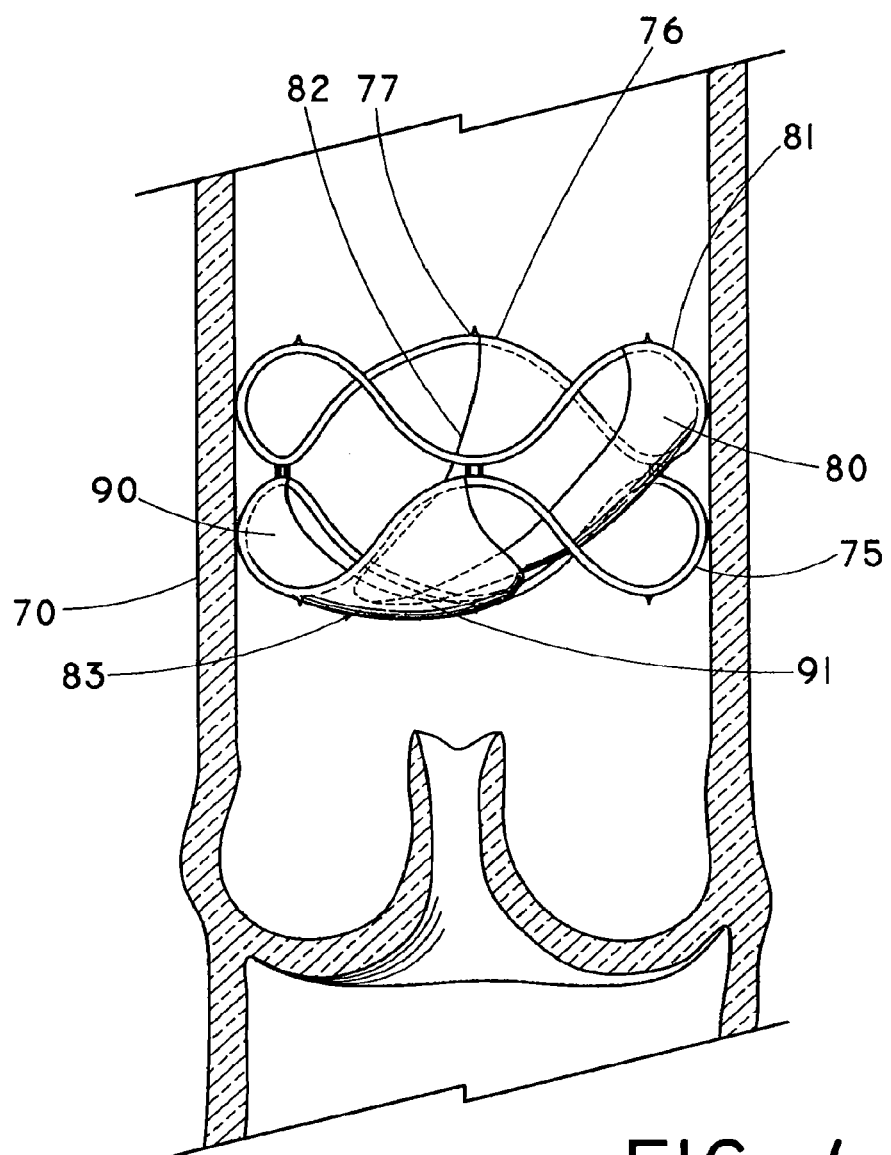
FIG. 4 is a partially sectioned view of a body vessel containing a flow-deflecting medical device according to a second example, located proximal to a native valve.

In an alternative example, the medical device can be configured such that a first flow-deflecting member may contact and/or substantially seal against a second flow-deflecting member in the second position, such that valve is created during retrograde flow conditions. For example, FIG. 4 shows a partially sectioned view of a body vessel 70 containing a medical device comprising a support structure 75, a first flow-deflecting member 80, and a second flow-deflecting member 90. A first, attached edge 81 of the first flow-deflecting member 80 is attached to a first support structure portion 76, terminating at or near a support structure apex 77. In other examples, the flow-deflecting member(s) support structure attachment may terminate at a support structure nadir (e.g., FIG. 5) or any other suitable portion of the support structure.

A second free edge 82 of the first flow-deflecting member 80 is free of the support structure 75, permitting the first flow-deflecting member 80 to be responsive to the direction of fluid flow in a body vessel 70. The free edge 82 of the first flow-deflecting member 80 may contact or substantially seal 83 against the retrograde flow-receiving surface 91 of the second flow deflecting member 90 in the second position, thereby at least partially obstructing, delaying, and/or reducing retrograde flow in the body vessel.

Figure 5:
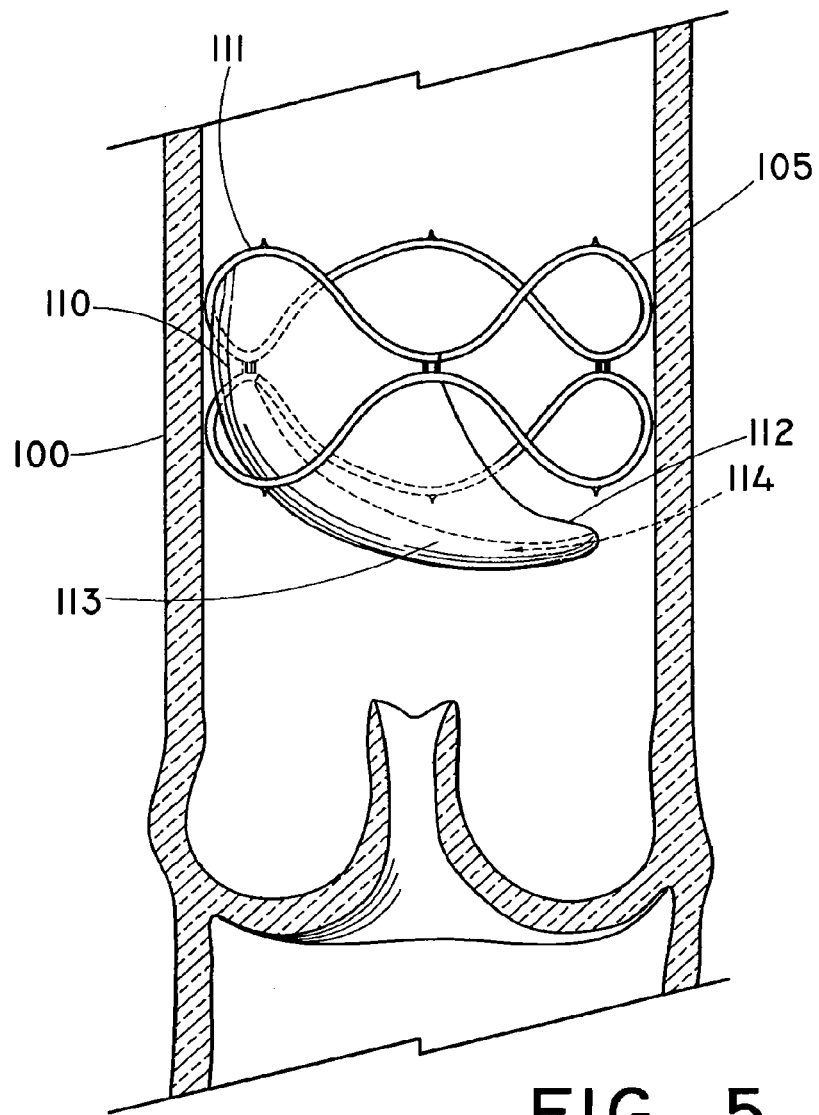
FIG. 5 is a partially sectioned view of a body vessel containing a flow-deflecting medical device according to another example, located proximal to a native valve.

In a further example, the medical device may comprise a single flow-deflecting member for redirecting retrograde flow. FIG. 5 shows a partially sectioned view of a blood vessel 100 containing a medical device comprising a support structure 105 and a flow-deflecting member 110 in the second position. The flow-deflecting member has 110 a first attached edge 111 attached to the support structure 105 and a second free edge 112 that is free of the support structure 105. The free edge 112 permits the flow-deflecting member 110 to be responsive to the direction of fluid flow in a body vessel. For example, antegrade flow may contact an antegrade flow-receiving surface 113 of the flow-deflecting member 110, urging the flow-deflecting member free edge 112 proximally in the body vessel, such that the free edge 112 is proximal to the attached edge 111. Retrograde flow may contact a retrograde flow-receiving surface 114 of the flow-deflecting member, urging the flow-deflecting member free edge 112 distally in the body vessel, such that the free edge 112 is distal to the attached edge 111.

The flow-deflecting medical devices depicted in FIGS. 4 and 5 are preferably configured to include sufficient slack and flexibility to evert and invert such that an orifice is sized to allow sufficient antegrade flow, while receiving and deflecting retrograde flow.

Although flow-deflecting medical devices in the illustrative figures are shown with a single or two flow-deflecting members, the medical device may include any suitable number of flow-deflecting members. The flow-deflecting member(s) need only be able to provide the functionality described herein. The specific number chosen will depend on several factors, including the type and configuration of the support structure. For example, the medical device may comprise 2, 3, 4, 5, 6, 7, 8, or more flow-deflecting members.

A wide variety of materials acceptable for use as flow-deflecting members are known in the art, and any suitable material can be utilized. Examples of suitable materials include natural materials, and synthetic materials.

Examples of suitable natural materials include collagen and extracellular matrix (ECM) material, such as submucosa. The "extracellular matrix" is typically a collagen-rich substance that is found in between cells in animal tissue and serves as a structural element in tissues. Such an extracellular matrix is preferably a complex mixture of polysaccharides and proteins secreted by cells. The extracellular matrix can be isolated and treated in a variety of ways. Following isolation and treatment, it is referred to as an ECM. ECM may be isolated from submucosa (including small intestine submucosa), stomach submucosa, urinary bladder submucosa, tissue mucosa, renal capsule, dura mater, liver basement membrane, pericardium or other tissues. One specific example of ECM is small intestine submucose (SIS), available from Cook Biotech, West Lafayette, Ind. When implanted, SIS can undergo remodeling and can induce the growth of endogenous tissues upon implantation into a host. SIS has been used successfully in vascular grafts, urinary bladder and hernia repair, replacement and repair of tendons and ligaments, and dermal grafts. SIS is particularly well-suited for use as valve members, such as leaflets.

In addition to xenogenic biomaterials, such as SIS, autologous tissue can be harvested as well. Additionally Elastin or Elastin Like Polypetides (ELPs) and the like offer potential as a material to fabricate the flexible covering or discrete shaping members to form a device with exceptional biocompatibility. Another alternative is use of allographs such as harvested native valve tissue. Such tissue is commercially available in a cryopreserved state.

Examples of suitable polymeric materials include polyesters, such as poly(ethylene terephthalate), polylactide, polyglycolide and copolymers thereof; fluorinated polymers, such as polytetrafluoroethylene (PTFE), expanded PTFE and poly (vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances.

The valve member may be made of one or more polymers that do not require treatment or modification to be biocompatible. More desirably, the valve member includes a biocompatible polyurethane. One example of a biocompatible polyurethane, THORALON (THORATEC, Pleasanton, Calif.), has been used in certain vascular applications and is characterized by thromboresistance, high tensile strength, low water absorption, low critical surface tension and good flex life.

A variety of other biocompatible polyurethanes/polycarbamates and urea linkages (hereinafter "—C(O)N or CON type polymers") also may be employed. Biocompatible CON type polymers modified with cationic, anionic and aliphatic side chains also may be used. See, for example, U.S. Pat. No. 5,017,664, which is incorporated herein by reference in its entirety.

Other biocompatible CON type polymers include: segmented polyurethanes, such as BIOSPAN; polycarbonate urethanes, such as BIONATE; polyetherurethanes, such as ELASTHANE; (all available from POLYMER TECHNOLOGY GROUP, Berkeley, Calif.); siloxane-polyurethanes, such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes, such as PURSIL-10, -20, and -40 TSPU; PTMO and PDMS polyether-based aliphatic siloxane-polyurethanes, such as PURSIL AL-5 and AL-10 TSPU; aliphatic, hydroxy-terminated polycarbonate and PDMS polycarbonate-based siloxane-polyurethanes, such as CARBOSIL-10, -20, and -40 TSPU (all available from POLYMER TECHNOLOGY GROUP). Examples of siloxane-polyurethanes are disclosed in U.S. Pat. Application Publication No. 2002/0187288 A1, which is incorporated herein by reference in its entirety.

In addition, any of these biocompatible CON type polymers may be endcapped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference in its entirety.

Support Structure

A wide variety of support structures are known in the medical technology arts, and any suitable support structure may be utilized. Suitable support structures can have a variety of configurations, including braided strands, helically wound strands, ring members, consecutively attached ring members, sinusoidal members, and zig-zag members.

Suitable support structures can have a variety of sizes. The exact configuration and size chosen will depend on several factors, including the desired delivery technique, the nature of the vessel in which the device will be implanted, and the size of the vessel.

For example, suitable support structures capable or supporting one or more flow-deflecting members are disclosed in U.S. Pat. No. 6,464,720 to Boatman et al. for a RADIALLY EXPANDABLE STENT; U.S. Pat. No. 6,231,598 to Berry et al. for a RADIALLY EXPANDABLE STENT; U.S. Pat. No. 6,299,635 to Frantzen for a RADIALLY EXPANDABLE NON-AXIALLY CONTRACTING SURGICAL STENT; U.S. Pat. No. 4,580,568 to Gianturco for a PERCUTANEOUS ENDOVASCULAR STENT AND METHOD FOR INSERTION THEREOF; U.S. Publication No. 20010039450 to Pavcnik et al. for an IMPLANTABLE VASCULAR DEVICE; U.S. Pat. No. 5,800,508 to Goicoechea et al. for a BIFURCATED ENDOLUMINAL PROSTHESIS; U.S. Pat. No. 5,665,115 to Cragg for an INTRALUMINAL STENT; U.S. Pat. No. 5,507,767 to Maeda et al. for a SPIRAL STENT; and U.S. Pat. No. 6,508,833 to Pavcnik et al. for a MULTIPLE-SIDED INTRALUMINAL MEDICAL DEVICE, each of which is hereby incorporated by reference in its entirety for the purpose of describing suitable support structures for use in medical devices according to the disclosure. A support structure and configuration can be chosen to facilitate maintenance of the device in the vessel following implantation.

In one example, the support structure configuration comprises interconnected serpentine support structure sections. For example, FIG. 1 depicts an exemplary support structure configuration comprising a first 11 and second 12 serpentine support structure portions attached to one another by struts 13. The first 11 and second 12 support structure portions each includes three bends oriented proximally and three distally with the flow-deflecting members 20, 30 attached thereabout. In one example, the flow deflecting members 20, 30 are attached such that the free edges 22, 32 span two adjacent distally oriented bends. Alternatively, the flow deflecting members 80, 90 may span two adjacent proximally oriented bends, as depicted in FIG. 4.

Figure 6:
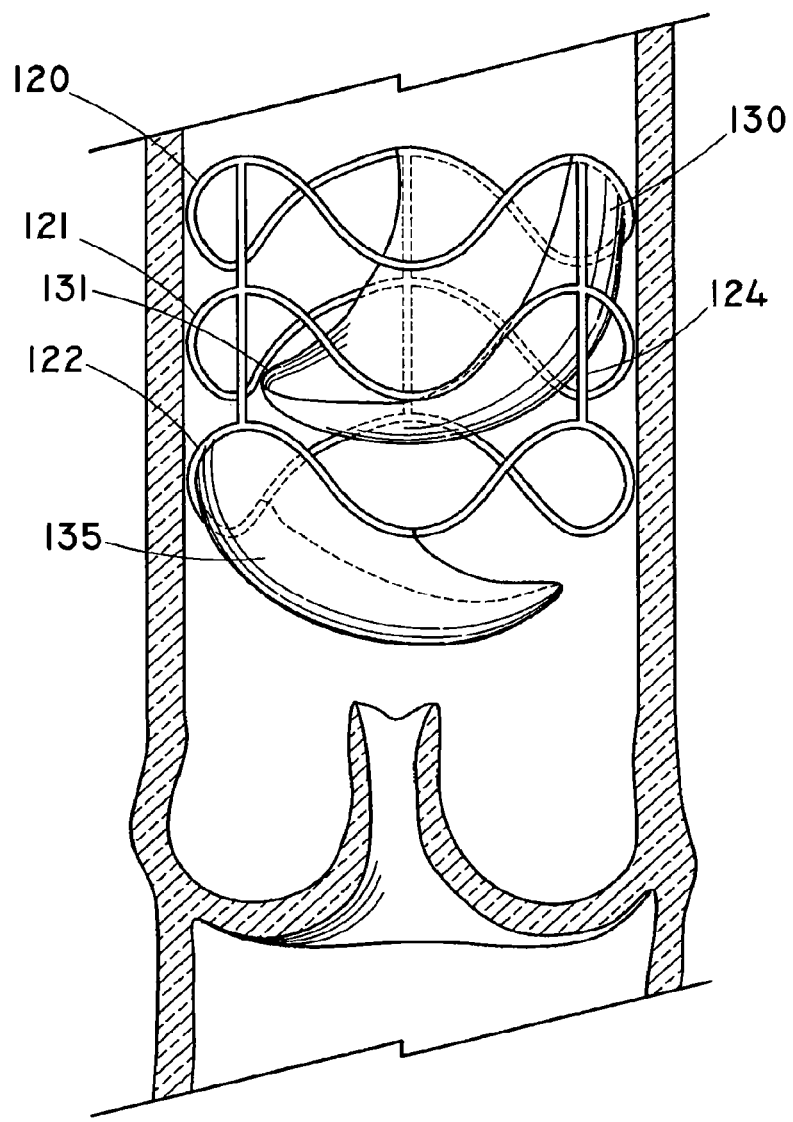
FIG. 6 is a partially sectioned view of a body vessel containing a flow-deflecting medical device according to a further example, located proximal to a native valve.

In another example, shown in FIG. 6, the serpentine support structure portions 120, 121, 122 may be aligned with one another and interconnected by longer struts 124. The first flow-deflecting member 130 is attached to the first support structure portion 120 with the free edge 131 spanning distally oriented bends. Optionally, a third support structure portion 121 may be disposed between the first support structure portion 120 bearing the first flow-deflecting member 130 and the second support structure portion 122 bearing the second flow-deflecting member 135.

Figure 7:
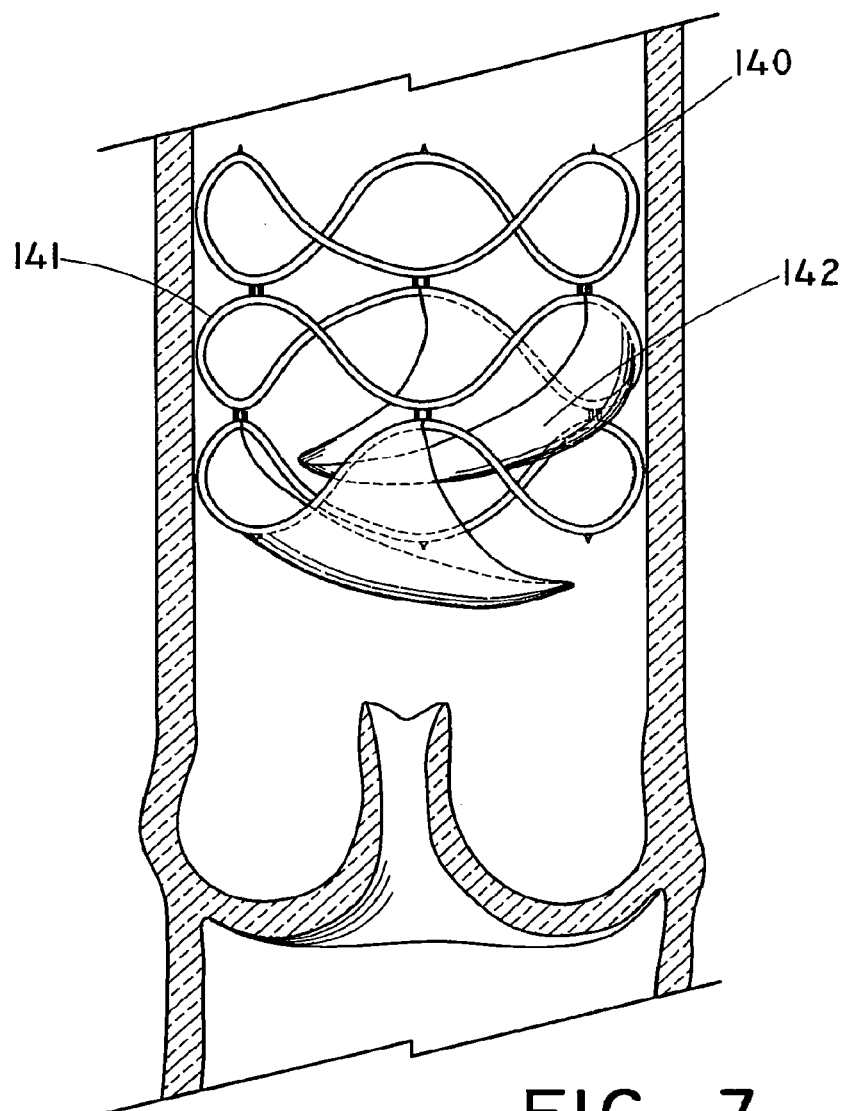
FIG. 7 is a partially sectioned view of a body vessel containing a flow-deflecting medical device according to another example, located proximal to a native valve.

Additional support structure configurations are possible as well, including, but not limited to, additional or fewer serpentine bends in the support structure portion, additional interconnecting structures, and additional support structure portions. For example, FIG. 7 depicts a third support structure portion 140 located proximal to the first support structure portion 141 bearing the first flow-deflecting member 142.

Suitable support structures may be made from one or more suitable materials and need only be biocompatible or able to be made biocompatible. Support structure material that is too stiff may damage the vessel, not conform well to the vessel wall, and/or increase the profile of the device when loaded in a delivery system prior to deployment. Support structure material that is not sufficiently stiff may not allow the flow-deflecting members to function as desired.

Examples of suitable materials include, without limitation, stainless steel, nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and/or composites or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylenestyrene block copolymer (Kraton), polyethylene teraphthalate, polyurethane, polyamide, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as, polylactic acid, polyglycolic acid or copolymers thereof, a polyanhydride, polycaprolactone, polyhydroxybutyrate valerate or other biodegradable polymer, or mixtures or copolymers thereof; extracellular matrix components, proteins, collagen, fibrin or other therapeutic agent, or mixtures thereof. Desirably, the support structure material includes stainless steel or nitinol.

In one example, the support structure comprises compressed and expanded configurations. The support structure may expand from a compressed, or unexpanded, delivery configuration to one or more radially expanded deployment configurations, for example through self expansion or balloon expansion of the support structure. The expanded configuration can have any suitable cross-sectional configuration, including circular or elliptical. In one example, the support structure can be oriented along the longitudinal axis of a body vessel in the expanded or compressed configurations. In some examples, the expanded configurations can be resiliently further extended in one or more radial directions.

The support structure may be self-expanding or balloon expandable. Upon compression, self-expanding support structures can expand toward their precompression geometry. In some examples, a self-expanding support structure can be compressed into a low-profile delivery conformation and then constrained within a delivery system for delivery to a point of treatment in the lumen of a body vessel. At the point of treatment, the self-expanding support structure can be released and allowed to subsequently expand to another configuration.

The dimensions of the implantable support structure will depend on its intended use. Typically, the collapsed dimension of the support structure will usually be in the range from about 1 mm to 10 mm, more usually being in the range from 1.5 mm to 6 mm for vascular applications. The expanded dimension will usually be in the range from about 2 mm to 30 mm, preferably being in the range from about 2.5 mm to 18 mm for vascular applications.

The support structure also may include a means for orienting the support structure within a body lumen. For example, the support structure can comprise a marker, such as a radiopaque portion of the support structure that would be seen by remote imaging methods including X-ray, ultrasound, Magnetic Resonance Imaging and the like, or by detecting a signal from or corresponding to the marker. In other examples, the delivery device can comprise a support structure with indicia relating to the orientation of the support structure within the body vessel. In other examples, indicia can be located, for example, on a portion of a delivery catheter that can be correlated to the location of the support structure within a body vessel.

A support structure or delivery device may comprise one or more radiopaque materials to facilitate tracking and positioning of the medical device, which may be added in any fabrication method or absorbed into or sprayed onto the surface of part or all of the medical device. The degree of radiopacity contrast can be altered by implant content. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platium, iridium, and rhodium. Radiopacity is typically determined by fluoroscope or x-ray film.

Attachment in Body Vessel

Flow-deflecting medical devices may optionally include supplemental attachment means such as anchoring devices, proximal or distal stents, suturing, stapling, searing, bonding, gluing, or otherwise adhering the medical device to the vessel wall or combinations thereof. For example, the medical device may be secured in place with one or more anchoring devices.

A wide variety of structural features may be used in medical devices as anchoring devices, and any suitable structural feature can be used. For example, individual barbs may be used to implant the prosthetic valve into the vessel. The barbs may be secured to the medical device by any means known to one skilled in the art, including but not limited to welding, stitching, bonding, and adhesives. In one example, shown in FIG. 1, barbs 14 may be attached to the medical device support structure 10.

Furthermore, barbs can also comprise separate members attached to the medical device by suitable attachment means. For instance, barbs can be formed by V-shaped cuts transversing the thickness of a flat metal support structure, which are bent outward to form the barb. In some examples, the number, arrangement, and configuration of the integral barbs can vary according to design preference and the clinical use of the device. The barbs can have any suitable shape, including points or "fish hook"-like configurations. The barbs may or may not penetrate the vein wall, depending on their design and other factors, including the thickness and type of covering used.

Alternatively or in addition to anchoring devices, bioadhesives may be used for attachment. The bioadhesive can be included in any suitable part of the medical device. Selection of the type of bioadhesive, the portions of the medical device comprising the bioadhesive, and the manner of attaching the bioadhesive to the medical device can be chosen to perform a desired function upon implantation. For example, the bioadhesive can be selected to promote increased affinity of the desired portion of prosthetic valve to the section of the body vessel against which it is urged.

Bioadhesives for use in conjunction with the present disclosure include any suitable bioadhesives. For example, appropriate bioadhesives include, but are not limited to, the following: (1) cyanoacrylates such as ethyl cyanoacrylate, butyl cyanoacrylate, octyl cyanoacrylate, and hexyl cyanoacrylate; (2) fibrinogen, with or without thrombin, fibrin, fibropectin, elastin, and laminin; (3) mussel adhesive protein, chitosan, prolamine gel and transforming growth factor beta (TGF-B); (4) polysaccharides such as acacia, carboxymethyl-cellulose, dextran, hyaluronic acid, hydroxypropyl-cellulose, hydroxypropyl-methylcellulose, karaya gum, pectin, starch, alginates, and tragacanth; (5) polyacrylic acid, polycarbophil, modified hypromellose, gelatin, polyvinylpylindone, polyvinylalcohol, polyethylene glycol, polyethylene oxide, aldehyde relative multifunctional chemicals, maleic anhydride co-polymers, and polypeptides; and (6) any bioabsorbable and biostable polymers derivitized with sticky molecules such as arginine, glycine, and aspartic acid, and copolymers.

Furthermore, commercially available bioadhesives that may be used include, but are not limited to: FOCALSEAL® (biodegradable eosin-PEGlactide hydrogel requiring photopolymerization with Xenon light wand) produced by Focal; BERIPLAST® produced by Adventis-Bering; VIVOSTAT® produced by ConvaTec (Bristol-Meyers-Squibb); SEALAGEN™ produced by Baxter; FIBRX® (containing virally inactivated human fibrinogen and inhibited-human thrombin) produced by CryoLife; TISSEEL® (fibrin glue composed of plasma derivatives from the last stages in the natural coagulation pathway where soluble fibrinogen is converted into a solid fibrin) and TISSUCOL® produced by Baxter; QUIXIL® (Biological Active Component and Thrombin) produced by Omrix Biopharm; a PEG-collagen conjugate produced by Cohesion (Collagen); HYSTOACRYL® BLUE (ENBUCRILATE) (cyanoacrylate) produced by Davis & Geck; NEXACRYL™ (N-butyl cyanoacrylate), NEXABOND™, NEXABOND™ S/C, and TRAUMASEAL™ (product based on cyanoacrylate) produced by Closure Medical (TriPoint Medical); DERMABOND® which consists of 2-octyl cyanoacrylate produced as DERMABOND® by (Ethicon); TISSUEGLU® produced by Medi-West Pharma; and VETBOND® which consists of n-butyl cyanoacrylate produced by 3M.

Bioactive Agents

Optionally, the flow-deflecting medical device can include one or more bioactive agents. The bioactive agent can be included in any suitable part of the medical device. Selection of the type of bioactive, the portions of the medical device comprising the bioactive agent, and the manner of attaching the bioactive agent to the medical device can be chosen to perform a desired function upon implantation. For example, the bioactive material can be selected to treat indications such as coronary artery angioplasty, renal artery angioplasty, carotid artery surgery, renal dialysis fistulae stenosis, or vascular graft stenosis.

The bioactive materials can be attached to the flow-deflecting medical device in any suitable manner. For example, a bioactive can be combined with a biocompatible polyurethane, impregnated in the flow-deflecting members, or attached to the surface of the medical device.

The bioactive agent can be selected to perform one or more desired biological functions. For example, the medical device support structure may comprise a bioactive selected to promote the ingrowth of tissue from the interior wall of a body vessel, such as a growth factor. An anti-angiogenic or antneoplastic bioactive such as paclitaxel, sirolimus, or a rapamycin analog, or a metalloproteinase inhibitor such as batimastaat can be incorporated in or coated on the support structure to mitigate or prevent undesired conditions in the vessel wall, such as restenosis. Many other types of bioactive agents can be incorporated in the medical device.

Bioactive materials for use in biocompatible coatings include those suitable for coating an implantable medical device. The bioactive agent can include, for example, one or more of the following: antiproliferative agents (sirolimus, paclitaxel, actinomycin D, cyclosporine), immunomodulating drugs (tacrolimus, dexamethasone), metalloproteinase inhibitors (such as batimastat), antisclerosing agents (such as collagenases, halofuginone), prohealing drugs (nitric oxide donors, estradiols), mast cell inhibitors and molecular interventional bioactive agents such as c-myc antisense compounds, thromboresistant agents, thrombolytic agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Other useful bioactive agents include, for example, viral vectors and growth hormones such as Fibroblast Growth Factor and Transforming Growth Factor-.beta.

Flow-deflecting medical devices comprising an antithrombogenic bioactive agent are particularly preferred for implantation in areas of the body that contact blood. For example, an antithromogenic bioactive agent can be coated on the flow-deflecting member surfaces. An antithrombogenic bioactive agent is any bioactive agent that inhibits or prevents thrombus formation within a body vessel. The medical device can comprise any suitable antithrombogenic bioactive agent. Types of antithrombotic bioactive agents include anticoagulants, antiplatelets, and fibrinolytics. Anticoagulants are bioactive materials which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid is dissolution of a thrombus. Examples of antithrombotics include but are not limited to anticoagulants such as thrombin, Factor Xa, Factor Vila and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

The flow-deflecting medical devices also may include a thrombolytic bioactive agent. In one example, the thrombolytic bioactive agent is positioned on or within the flow-deflecting members. Thrombolytic agents are used to dissolve blood clots that may adversely affect blood flow in body vessels. A thrombolytic agent is any therapeutic agent that either digests fibrin fibres directly or activates the natural mechanisms for doing so. The medical device can comprise any suitable thrombolytic agent. Examples of commercial thrombolytics, with the corresponding active agent in parenthesis, include, but are not limited to, Abbokinase (urokinase), Abbokinase Open-Cath (urokinase), Activase (alteplase, recombinant), Eminase (anitstreplase), Retavase (reteplase, recombinant), and Streptase (streptokinase). Other commonly used names are anisoylated plasminogen-streptokinase activator complex; APSAC; tissue-type plasminogen activator (recombinant); tPA; rt-PA.

A bioactive agent can be incorporated in or applied to portions of the medical device by any suitable method that permits adequate retention of the bioactive agent material and the effectiveness thereof for an intended purpose upon implantation in the body vessel. The configuration of the bioactive agent on or in the medical device will depend in part on the desired rate of elution for the bioactive. Bioactive agents can be coated directly on the medical device surface or can be adhered to a medical device surface by means of a coating. For example, an antithrombotic bioactive agent can be blended with a polymer and spray or dip coated on the device surface. For example, a bioactive agent material can be posited on the surface of the medical device and a porous coating layer can be posited over the bioactive agent material. The bioactive agent material can diffuse through the porous coating layer. The coating layer can also be nonporous wherein the rate of diffusion of the bioactive agent material through the coating layer is controlled by the rate of dissolution of the bioactive agent material in the coating layer.

Flow-Deflecting Medical Device Delivery

Flow-deflecting medial devices can be configured for delivery to a body vessel. For example, a medical device can be compressed to a delivery configuration within a retaining sheath that is part of a delivery system, such as a catheter-based system. Upon delivery, the medical device can be expanded, for example, by inflating a balloon from inside the medical device. The delivery configuration can be maintained prior to deployment of the medical device by any suitable means, including a sheath, a suture, a tube or other restraining material around all or part of the compressed medical device, or other methods.

In one example, the flow-deflecting medical device may be deployed in a body vessel proximal to a native valve. For example, FIGS. 2A and 3A depict a flow-deflective medical device 1 deployed in a body vessel 2 and positioned immediately proximal to a native venous valve 3.

Figure 8A:
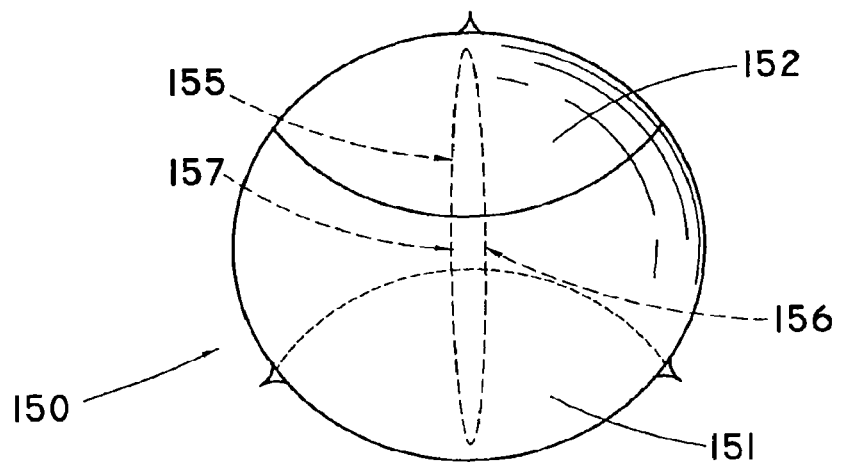
FIG. 8A is a top view of a body vessel containing an exemplary flow deflecting member, located proximal to a native valve, oriented with reference to the native valve.

The flow-deflecting medical device may be oriented in a body vessel such that the distal flow-deflecting member directs retrograde flow over both leaflets of a native bicuspid valve. For example, FIG. 8A shows a flow-deflecting medical device 150 comprising a first, proximal flow-deflecting member 151 and a second, distal flow-deflecting member 152. The medical device 150 is positioned proximal to a native bicuspid valve 155 having first 156 and second 157 leaflets. Retrograde fluid flow is deflected by the second flow-deflecting member evenly onto both the first leaflet 156 and the second leaflet 157 of the native valve 155. In this example, the first leaflet 156 and the second leaflet 157 equally share the weight or force of any retrograde flow.

Figure 8B:
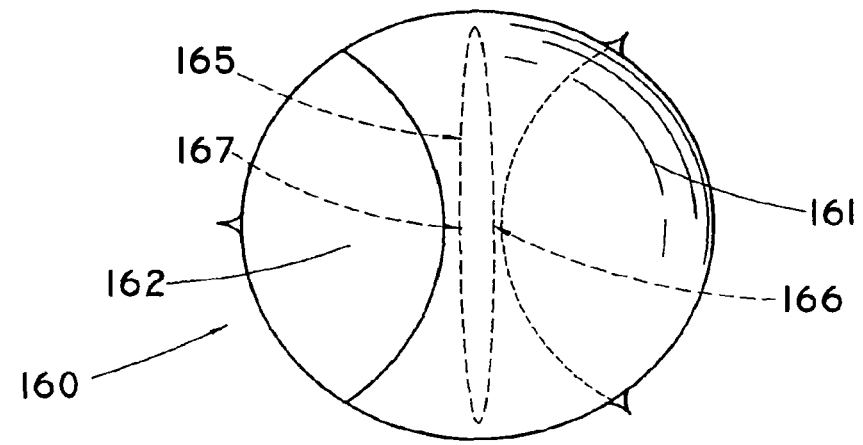
FIG. 8B is a top view of a body vessel containing another exemplary flow deflecting member, located proximal to a native valve, oriented with reference to the native valve.

In another example, the flow-deflecting member may be oriented in a body vessel such that retrograde flow is directed onto a single side of a native valve. For example, FIG. 8B depicts a flow-deflecting medical device 160 comprising a first, proximal flow-deflecting member 161 and a second, distal flow-deflecting member 162. The medical device 160 is positioned proximal to a native bicuspid valve 165 having first 166 and second 167 leaflets. Retrograde fluid flow is deflected by the second flow-deflecting member onto the first leaflet 166. In this example, the first leaflet 166 is subject to most of the weight or force of any retrograde flow.

Flow-deflecting medical devices can be deployed in a body lumen by means appropriate to their design. For example, flow-deflecting medical devices may be surgically implanted or be adapted for deployment using percutaneous transluminal catheter devices. The medical devices are designed for deployment by any of a variety of in situ expansion means.

The medical device may be mounted onto a catheter that holds the device as it is delivered through the body lumen and then releases the medical device and allows it to self-expand into contact with the body lumen. This deployment is effected after the medical device has been introduced percutaneously, transported transluminally and positioned at a desired location by means of the catheter. The self-expanding medical device may be deployed according to well-known deployment techniques for self-expanding medical devices. For example, the medical device may be positioned at the distal end of a catheter with a removable sheath or sleeve placed over the medical device to hold the device in a contracted state with a relatively small diameter. The medical device may then be implanted at the point of treatment by advancing the catheter over a guidewire to the location of the lesion and then withdrawing the sleeve from over the device. The medical device will automatically expand and exert pressure on the wall of the blood vessel at the site of the lesion. The catheter, sleeve, and guidewire may then be removed from the patient.

A bioabsorbable suture or sheath may be used to maintain a self-expanding flow-deflecting medical device in a compressed configuration both pri- or to and after deployment. As the bioabsorbable sheath or suture is degraded by the body after deployment, the medical device can expand within the body vessel. In some examples, a portion of the device can be restrained with a bioabsorbable material and another portion allowed to expand immediately upon implantation. For example, a self-expanding support structure can be partially restrained by a bioabsorbable material upon deployment and later expand as the bioabsorbable material is absorbed.

In another example, the medical device is first positioned to surround a portion of an inflatable balloon catheter. The medical device, with the balloon catheter inside is configured at a first, collapsed diameter. The device and the inflatable balloon are percutaneously introduced into a body lumen, following a previously positioned guidewire. For example, in rapid exchange, a rapid exchange prosthesis delivery balloon catheter allows exchange from a balloon angioplasty catheter to a device delivery catheter without the need to replace the angioplasty catheter guide wire with an exchange-length wire guide before exchanging the catheters. The device may be tracked by a fluoroscope, until the balloon portion and associated prosthetic valve are positioned within the body passageway at the point where the medical device is to be placed. Thereafter, the balloon is inflated and the medical device is expanded by the balloon portion from the collapsed diameter to a second expanded diameter. After the medical device has been expanded to the desired final expanded diameter, the balloon is deflated and the catheter is withdrawn, leaving the medical device in place. The medical device may be covered by a removable sheath during delivery to protect both the prosthesis and the vessels.

While the terms "contracted" and "compressed" have been used to describe the prosthetic valve as having the small diameter necessary for delivery to an implantation site, it will be appreciated that the terms, especially as applied to pressure-expandable prosthetic valves, should not be used to imply that the tube is under external pressure to provide the tube with a small diameter; i.e., a "contracted" or "compressed" pressure-expandable prosthetic valve may be formed and naturally reside in the "contracted" or "compressed" state until internally pressurized to expand. Therefore, "contracted" and "compressed" are intended only to imply that the prosthetic valve is in a state of having a small diameter relative to an expanded state. It will therefore be appreciated by those skilled in the art that yet other modifications could be made to the provided disclosure without deviating from its spirit and scope as so claimed.

Methods for delivering a prosthetic valve as described herein to any suitable body vessel are also provided, such as a vein, artery, biliary duct, ureteral vessel, body passage or portion of the alimentary canal.

Methods of Treatment and Prevention

Still other examples provide methods of treating a subject, which can be animal or human, comprising the step of providing one or more flow-deflecting medial devices, as described herein. In some examples, methods of treatment also may provide the step of delivering a flow-deflecting medical device to a point of treatment in a body vessel, or deploying a medical device at the point of treatment, wherein the medical devices are as described herein.

The disclosure also provides methods of treating a patient. In one example the method comprises a step of delivering a flow-deflecting medical device as described herein to a point of treatment in a body vessel, and deploying the medical device at the point of treatment. The delivering step can comprise delivery by surgical or by percutaneous delivery techniques known to those skilled in the art.

Methods for treating and/or preventing certain conditions are also provided, such as venous valve insufficiency, varicose veins, esophageal reflux, restenosis or atherosclerosis. In some examples, the disclosure relates to methods of treating venous valve-related conditions.

While various aspects and examples have been described, it will be apparent to those of ordinary skill in the art that many more examples and implementations are possible within the scope of the disclosure. Accordingly, the disclosure is not to be restricted except in light of the attached claims and their equivalents.

We claim:

1. A medical device for implantation in a body vessel, comprising:
   a support structure having compressed and expanded configurations, a lengthwise axis, first and second opposing sides relative to the lengthwise axis, a first support structure portion positioned on the first side, and a second support structure portion positioned on the second side and distal to the first support structure portion, the support structure defining a lumen; and
   first and second flow-deflecting members attached to the support structure;
   the first flow-deflecting member having a first edge attached to the first support structure portion and a second edge free of the support structure, the first flow-deflecting member movable between first and second positions;
   the second flow-deflecting member having a third edge and a fourth edge, the third edge attached to the second support structure portion such that the third edge is positioned distal to the first support structure portion and the first edge of the first flow-deflecting member relative to the lengthwise axis of the support structure, the fourth edge being free of the support structure;
   the second and fourth edges extending across the lumen and creating a central orifice;
   wherein retrograde flow in said body vessel contacts the first flow-deflecting member and urges the first flow-deflecting member into the second position to contact and substantially seal against the second flow-deflecting member; and
   wherein a portion of the second edge of the first flow-deflecting member is positioned opposite the first edge of the first flow-deflecting member and a portion of the fourth edge of the second flow-deflecting member relative to the lengthwise axis of the support frame when the first flow-deflecting member is in the second position.

2. The medical device of claim 1, wherein each of the first and second flow-deflecting members comprises a material selected from the group consisting of polymeric material, extracellular matrix material, xenogenic biomaterial, autologous tissue, and allogeneic tissue.

3. The medical device of claim 1, wherein at least one of the first and second flow-deflecting members comprises a natural material.

4. The medical device of claim 3, wherein the natural material comprises an extracellular matrix material.

5. The medical device of claim 4, wherein the extracellular matrix material comprises submucosa.

6. The medical device of claim 5, wherein the submucosa comprises small intestine submucosa.

7. The medical device of claim 3, wherein the natural material comprises allograph tissue.

8. The medical device of claim 7, wherein the allograph tissue comprises native valve tissue.

9. The medical device of claim 3, wherein the natural material comprises autologous tissue.

10. The medical device of claim 1, wherein at least one of the first and second flow-deflecting members comprises a synthetic material.

11. The medical device of claim 10, wherein the synthetic material comprises a polymeric material.

12. The medical device of claim 11, wherein the polymeric material is selected from the group consisting of polyurethane, polyethylene terephthlate, and polytetrafluoroethylene.

13. The medical device of claim 11, wherein the at least one of the first and second flow-deflecting members comprises a dipped or sprayed polymeric material.

14. The medical device of claim 1, wherein the support structure comprises at least two interconnected stents.

15. The medical device of claim 14, wherein each of the at least two interconnected stents comprises a stent having a serpentine configuration.

16. The medical device of claim 1, wherein the first flow-deflecting member is biased to the first position.

17. The medical device of claim 1, wherein the first flow-deflecting member is biased to the second position.

18. The medical device of claim 1, wherein the second flow-deflecting member is movable between third and fourth positions.

19. A medical device for implantation in a body vessel, comprising:
- a support structure having compressed and expanded configurations, a lengthwise axis, first and second opposing sides relative to the lengthwise axis, a first support structure portion positioned on the first side, and a second support structure portion positioned on the second side and distal to the first support structure portion, the support structure defining a lumen; and
- first and second flow-deflecting members attached to the support structure;
- the first flow-deflecting member having a first edge attached to the first support structure portion and a second edge free of the support structure, the first flow-deflecting member movable between a first position in which the first flow-deflecting member contacts and substantially seals against the second flow-deflecting member and a second position;
- the second flow-deflecting member having a third edge and a fourth edge, the third edge attached to the second support structure portion such that the third edge is positioned distal to the first support structure portion and the first edge of the first flow-deflecting member relative to the lengthwise axis of the support structure, the fourth edge being free of the support structure; and
- the second and fourth edges extending across the lumen and creating a central orifice;
- wherein a portion of the second edge of the first flow-deflecting member is positioned opposite the first edge of the first flow-deflecting member and a portion of the fourth edge of the second flow-deflecting member relative to the lengthwise axis of the support frame when the first flow-deflecting member is in the second position.

20. A medical device for implantation in a body vessel, comprising:
- a support structure having compressed and expanded configurations, a lengthwise axis, first and second opposing sides relative to the lengthwise axis, a first support structure portion positioned on the first side, and a second support structure portion positioned on the second side and distal to the first support structure portion, the support structure defining a lumen; and
- first and second flow-deflecting members attached to the support structure;
- the first flow-deflecting member having a first edge attached to the first support structure portion and a second edge free of the support structure, the first flow-deflecting member biased to a first position in which the first flow-deflecting member contacts and substantially seals against the second flow-deflecting member;
- the second flow-deflecting member having a third edge and a fourth edge, the third edge attached to the second support structure portion such that the third edge is positioned distal to the first support structure portion and the first edge of the first flow-deflecting member relative to the lengthwise axis of the support structure, the fourth edge being free of the support structure; and
- the second and fourth edges extending across the lumen and creating a central orifice;
- wherein a portion of the second edge of the first flow-deflecting member is positioned opposite the first edge of the first flow-deflecting member and a portion of the fourth edge of the second flow-deflecting member relative to the lengthwise axis of the support frame when the first flow-deflecting member is in the second position.

* * * * *